United States Patent [19]

Perricone

[11] Patent Number: 5,545,398
[45] Date of Patent: Aug. 13, 1996

[54] METHOD AND COMPOSITIONS FOR TOPICAL APPLICATION TO THE SKIN OF TOCOTRIENOL FOR PREVENTION AND/OR TREATMENT OF SKIN DAMAGE

[76] Inventor: Nicholos V. Perricone, 35 Pleasant St., Meriden, Conn. 06450

[21] Appl. No.: 361,737

[22] Filed: Dec. 21, 1994

Related U.S. Application Data

[63] Continuation-in-part of Ser. No. 3,603, Jan. 13, 1993, Pat. No. 5,376,361.

[51] Int. Cl.$^6$ ............................................. A61K 7/42
[52] U.S. Cl. ..................... 424/59; 514/456; 514/458; 514/474; 514/847
[58] Field of Search .............................. 424/59; 514/456, 514/458, 474, 847

[56] References Cited

U.S. PATENT DOCUMENTS

| | | |
|---|---|---|
| 4,695,452 | 9/1987 | Gannis et al. |
| 4,975,272 | 12/1990 | Voyt ..................................... 514/458 |

FOREIGN PATENT DOCUMENTS

| | | | |
|---|---|---|---|
| 45-23634 | 7/1970 | Japan | 514/474 |
| 51-73137 | 6/1976 | Japan | 514/458 |
| 0116616 | 6/1985 | Japan | 514/474 |
| 0166618 | 6/1985 | Japan | 514/474 |
| 1152613 | 7/1986 | Japan | 514/474 |
| 4686628 | 9/1875 | U.S.S.R. | 514/474 |

OTHER PUBLICATIONS

Derwent Abstract of EP92–917637, Jul. 30, 1992, Bonte et al.
Derwent Abstract of JP86–28625, Feb. 12, 1986, arakawa.
Derwent Abstract of JP61183206A, Aug. 15, 1986, Lion Corp.
Chem–Abs., vol. 119:152113, Lane et al.
Chem–Abs, vol. 115:68388, Junichi et al.
Burton, G. W., et al., J. Am. Chem. Soc. 107: 7073–7065 (1985).
The Merck Index, 11th ed., entries 9417–9423 and 9931 (1989).
Nakano., M., et al., Biochim. Biophys. Acta 619: 274–286 (1980).
Serbinova, E., et al., Free Radical Biology & Med. 10: 263–275 (1991).
Wilson, R., Drug and Cosmetic Industry, 32–34, 38 and 68 (Aug., 1992).

*Primary Examiner*—Shelley A. Dodson
*Attorney, Agent, or Firm*—St. Onge Steward Johnston & Reens

[57] ABSTRACT

A method for the prevention and/or treatment of skin or hair damage, particularly inflammation and aging of skin and hair damage from sunlight and chemicals, in which a tocotrienol, a derivative thereof or a vitamin E preparation enriched with tocotrienol or a tocotrienol derivative, is topically applied to the exposed or affected skin or hair areas. A fat-soluble fatty acid ester of ascorbic acid such as palmityl ascorbate is preferably applied with the tocotrienol in association with a dermatologically acceptable carrier.

20 Claims, No Drawings

METHOD AND COMPOSITIONS FOR TOPICAL APPLICATION TO THE SKIN OF TOCOTRIENOL FOR PREVENTION AND/OR TREATMENT OF SKIN DAMAGE

RELATED APPLICATION DATA

This is a continuation-in-part of U.S. patent application Ser. No. 08/003,603, filed Jan. 13, 1993, now U.S. Pat. No. 5,376,361.

TECHNICAL FIELD

The present invention relates to the topical application to the skin or hair of active agents, and/or preparations containing them, for the prevention and/or treatment of damage to skin, particularly for the treatment or prevention of inflammatory and aging effects, and hair, particularly for sunlight and chemical damage, using tocotrienols.

BACKGROUND ART

Vitamin E is a fat-soluble vitamin necessary in the diet of many species for normal reproduction, normal development of muscles, normal resistance of erythrocytes to hemolysis, and various other biochemical functions. The most widely accepted function of vitamin E is an an antioxidant, protecting polyunsaturated fatty acids in membranes and other cellular structures from attack by free radicals. Vitamin E occurs in cereals (especially wheat germ and corn), sunflower seed, rapeseed, soybean oil, alfalfa, lettuce, egg yolk, and beef liver, and consists primarily of three molecular species of tocol derivatives, the alpha-, beta- and gamma-tocopherols, of which alpha-tocopherol is most important because it has the widest distribution and greatest biological activity.

Other tocopherols have been found in nature, including gamma-, eta-, zeta$_2$, zeta$_1$- and epsilon-tocopherol. The last two species, which occur in cereal grains, have unsaturated hydrocarbon tails and have been recently called tocotrienols (denoted alpha- and beta-tocotrienol, respectively) because each has three double bonds in the side chain, and this nomenclature distinguishes them from tocopherols bearing saturated tails. Gamma-tocopherol is claimed to be the most potent antioxidant of any tocopherol species (*The Merck Index*, 11th ed., 1989, entries 9417 to 9423 and 9931), but activity appears to be dependent on the system used for measurement. Thus, in the in vitro systems of Burton, G. W., et al., *J. Am. Chem. Soc.* 107:7073–7065 (1985), for example, alpha-tocopherol was the most powerful antioxidant.

The antioxidant function of vitamin E per se is localized in the chromanol nucleus, where the phenolic hydroxy group donates a hydrogen atom to quench lipid radicals ibid., and Serbinova, E., et al., *Free Radical Biology & Med.*, 10:263–275 (1991)). The antioxidant potency of vitamin E is determined by the efficiency of the tocopherol in scavenging radicals and by the reactivity of the chromanoxyl radical formed in further propagation of lipid peroxidation or in the regeneration of the tocopherol due to interaction of the chromanoxyl radical with reductants; the latter does not propagate lipid peroxidation.

In homogenous solutions, the rate constants of the reaction between the chromanol nucleus and radicals do not depend upon the length or unsaturation of the tocopherol hydrocarbon tails, but mainly depend on the number of methyl groups in the benzene ring of the chromanol nucleus (Burton, G. W., et al., cited above). Similarly, the reactivity of the chromanoxyl radical is mainly determined by hindering effects of the methyl groups.

The situation is more complex in heterogenous membrane systems, however, where vitamin E appears to owe its antioxidant potency not solely to the chemistry of the tocopherol molecule but also to its mobility and accessibility within the membrane (Serbinova, cited above). In some systems, tocotrienols appear to have higher antioxidant activity (ibid.). However, in others, direct comparisons of antioxidant efficiency of tocopherols having saturated tails with tocotrienols did not demonstrate decisive differences in the activities of these two forms of vitamin E (ibid. and Nakano, M., et al., *Biochim. Biophys. Acta* 619:274–286 (1980)).

The antioxidant activity of tocotrienol prevents free radical damage to cells and cell components. Free radical damage is most evident in cellular membranes because of the density of the molecular structure of the membranes. It is currently hypothesized that cell membrane aging leads to all of the various cellular changes seen in aging, such as decreased RNA production, decreased protein production, and faulty enzyme action.

Inflammation in skin is mediated by several active chemicals and metabolites of arachidonic acid. Arachidonic acid is oxidized by cyclo-oxygenase and lipoxygenase to active metabolites such as the leukotrienes and 5- and 12- hydroxyeicosatetraenoic acid (HETES). Within the arachidonic acid cascade, many free radicals are generated, which both perpetuate and magnify the inflammatory cascade, resulting in skin damage and manifested clinically as erythema.

Early suggestions for dealing with erythema and aging effects in skin were predominantly aimed at lubrications and emollients through use of topical compositions containing soothing agents, e.g., as exemplified by commercial hand lotion products and the like. More recently, attention has been directed to agents which address the underlying processes involved in skin damage, such as the free radical generation processes. In this regard, investigations have been made with respect to the antioxidants vitamin E and vitamin C to quench free radicals on the surface of the skin and to protect lipid membranes intracellularly (Wilson, R., *Drug and Cosmetic Industry,* 32–34, 38, and 68, August 1992).

Damage to hair, particularly damage caused by excessive exposure to sunlight or harsh chemicals, is also mediated in part by oxidation of keratin. Traditional remedies typically add oil in a conditioner or shampoo to ameliorate the hair's dryness and brittleness.

It would be desirable to have alternative topical compositions for anti-inflammatory and anti-aging effects observed in skin, particularly compositions that are efficient in free radical scavenging in membranes. It would also be desirable to have hair treatments that treat the actual cause of hair damage, rather than merely assuage its effects.

DISCLOSURE OF THE INVENTION

The primary object of this invention is to provide methods and compositions for prevention and/or treatment of skin inflammation, aging, and other skin damage and hair damage mediated by free radicals.

It is a more particular object of the invention to provide a preventive regimen and/or therapy based upon topical application to exposed or affected skin areas or damaged hair of an active agent or precursor thereof, preferably in association with a dermatologically acceptable carrier or vehicle.

These and other objects are accomplished by the present invention, which provides a method and composition for the prevention and/or treatment of skin inflammation, aging and other skin damage and hair damage, which comprises topical application to the exposed or affected skin sites of an effective amount of one or more tocotrienols or derivatives thereof or vitamin E compositions enriched with tocotrienols or tocotrienol derivatives. Reductants such as alpha-hydroxy acids, ascorbic acid and the like, particularly fat-soluble fatty acid esters of ascorbic acid, can, optionally, be utilized along with the tocotrienol as a means for yet further enhancing the efficacy of the therapeutic or prophylactic treatment.

In the preferred practice of the invention, the tocotrienol (or derivative) or tocotrienol-enriched vitamin E is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin or hair areas. As noted, reductants, particularly ascorbyl fatty acid esters, e.g., ascorbyl palmitate, can be advantageously included in the compositions.

The amount of tocotrienol or derivative thereof (hereinafter referred to collectively as tocotrienol for ease of reference) necessary to bring about enhanced prevention and/or therapeutic treatment of skin or hair damage is not fixed per se, and necessarily is dependent upon the identity and form of tocotrienol employed, the concentration of tocotrienol when employed as a tocotrienol-enriched vitamin E preparation and/or with a carrier, the amount and type of any additional reductant such as ascorbyl fatty acid ester, when employed with the tocotrienol, the user's skin or hair type, and, where present, the severity and extent of the patient's pathological skin or hair condition. Generally, the tocotrienol or composition containing it is topically applied in effective amounts to skin areas which have been damaged or aged, or which are susceptible to damage, because of inflammation or aging, or hair that is dry and brittle.

BEST MODES FOR CARRYING OUT THE INVENTION

This invention is based upon the finding that tocotrienols or tocotrienol-enriched vitamin E compositions, especially tocotrienols or tocotrienol-enriched vitamin E in combination with a reductant, such as ascorbyl fatty acid ester, augment the efficacy of topical compositions for inflammation, aging and other skin damage, including compositions that contain conventional vitamin E. Tocotrienol also augments the efficacy of hair compositions.

As used herein, the term "tocopherol" encompasses vitamin E derivatives bearing saturated hydrocarbon tails having the following general formula:

thereof. The term "tocotrienol" encompasses their counterparts bearing unsaturated tails, including, but not limited to, alpha-, beta-, gamma-, and delta- tocotrienols, desmethyltocotrienol, didesmethyl-tocotrienol, occurring in sunflower seeds, vegetable oils, barley, brewer's grains, oat's, and African violets, which have three double bonds in the side chain at the 3', 7' and 11' positions in the formula set out above, their synthetic counterparts, their counterparts having methylated or demethylated chroman rings, and mixtures thereof. The double bonds may be cis or trans or mixtures thereof.

Tocotrienol or tocotrienol derivatives or mixtures thereof are employed in this invention either in the substantial absence of tocopherols wherein the compositions contain essentially no tocopherol or in tocotrienol-enriched vitamin E preparations. By "tocotrienol-enriched vitamin E preparations" is meant vitamin E preparations containing a greater concentration of tocotrienol than that found in preparations isolated from natural sources. These tocotrienol-enriched vitamin E preparations can, for example, be naturally-occurring vitamin E preparations to which tocotrienol has been added or naturally occurring vitamin E preparations from which a portion of tocopherol has been removed.

Preferred vitamin E preparations are isolated from natural sources, but synthetic preparations may also be employed as well as mixtures of natural and synthetic vitamin E. Tocotrienol-enriched vitamin E preparations may be obtained by fractionating vitamin E preparations to remove a portion of tocopherols and recover a preparation more highly concentrated in tocotrienol.

Many tocotrienols useful for the practice of the invention are natural products isolated, for example, from wheat germ oil, bran, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. D-alpha-tocotrienol is especially preferred in one embodiment.

As with other vitamin E preparations, tocotrienol or tocotrienol-enriched preparations include those containing tocotrienol and, in some cases, tocopherol derivatives, particularly stabilized derivatives. These typically include derivatives related to the phenolic hydroxyl functionality, i.e., wherein it is acylated with an organic acid to form an ester. Examples of such stabilized tocotrienols include, but are not limited to, tocotrienol acetate, tocotrienol succinate, and mixtures thereof. However, the derivatives may also include those involving other reactive groups known to those skilled in the art. Where tocotrienol derivatives are employed, they must be functionally equivalent to tocotrienol. Preferred derivatives contain both the chromanol nucleus and three double bonds in the hydrocarbon tail.

Vitamin E derivatives generally vary in consistency from viscous oils to oily liquids. Therefore, tocotrienols or tocotrienol-enriched vitamin E preparations can be applied neat

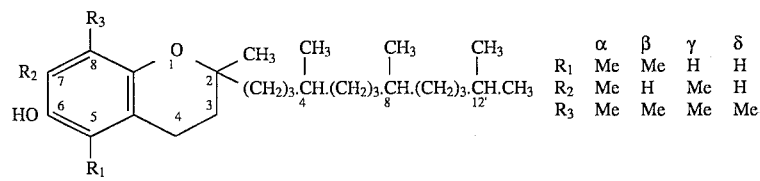

and includes both natural alpha-, beta-, gamma-, and delta-tocopherol as well as synthetic derivatives and mixtures to skin areas or hair subject to damage or already damaged. It is an advantage of the invention that the active compound is oily so that it physically contributes to the lubrication and soothing of affected skin areas, and to the replacement of natural oils on hair.

However, only effective amounts of tocotrienols are needed to prevent or treat skin or hair damage, so generally topical application to exposed or affected skin sites is accomplished in association with a carrier, and particularly one in which the active ingredient is soluble per se or is effectively solubilized (e.g., as an emulsion or microemulsion). It is necessary that the carrier be inert in the sense of not bringing about a deactivation of the tocotrienol or derivative, and in the sense of not bringing about any adverse effect on the skin areas to which it is applied.

Suitable carriers include water, alcohols, oils and the like, chosen for their ability to dissolve or disperse the active ingredient at concentrations of active ingredient most suitable for use in the preventive or therapeutic treatment. Generally, even low concentrations of active ingredient in a carrier will be suitable, requiring only that more frequent topical application be resorted to. As a practical matter, however, to avoid the need for repeated application, it is desirable that the topically applied composition (i.e., tocotrienol or derivative or tocotrienol-enriched vitamin E preparation plus carrier) be formulated to typically contain from about 0.025% to about 10% by weight, more narrowly about 0.025% to about 5% by weight, of the active ingredient. Some embodiments such as those for prophylaxis and compositions that remain on affected skin or hair for some time contain from about 0.025% to about 0.25% by weight, more narrowly from about 0.025% to about 0.1% by weight tocotrienol; others contain from about 0.05% to about 0.2%, more narrowly from about 0.05% to about 0.1% tocotrienol. Embodiments for treatment of more severe damage may contain from about 0.5% to about 3% by weight, more narrowly from about 0.5% to 1.5% by weight tocotrienol. Some embodiments contain at least about 3% by weight, typically at least about 3% to about 10% by weight, of the active ingredient. Carriers will accordingly be chosen which can solubilize or disperse the active ingredient at such concentrations.

While the carrier for the tocotrienol or derivative or tocotrienol-enriched vitamin E preparation can consist of a relatively simple solvent or dispersant such as water or oils, it is generally preferred that the carrier comprise a composition more conducive to topical application, and particularly one which will form a film or layer on the skin or hair to which it is applied so as to localize the application and provide some resistance to washing off by immersion in water or by perspiration and/or aid in the percutaneous delivery of the active agent. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

Carriers for hair compositions are also dermatologically acceptable so that the scalp is not injured. For damaged hair, tocotrienol is typically added to a shampoo, conditioner, hair cream, or hair spray or gel. Many of these compositons contain enriched palm oil. Tocotrienol is an excellent choice for these compositions as it not only acts as an antioxidant, but (as has been mentioned) it also replaces the natural hair oils. Levels of tocotrienol in hair compositions vary in different embodiments as set out above, and preferably vary from about 0.025% to about 1%. Treatments of extreme conditions, however, require more active ingredient.

Many preferred embodiments of this invention contain a reductant in addition to tocotrienol. Some embodiments, for example, employ alpha-hydroxy acids such as glycolic acid, hydroxymethylglycolic acid, lactic acid, glucuronic acid, galacturonic acid, gluconic acid, glucoheptonic acid, alpha-hydroxybutyric acid, alpha-hydroxyisobutyric acid, alpha-hydroxyvaleric acid, alpha-hydroxyisovaleric acid, alpha-hydroxycaproic acid, alpha-isocaproic acid, tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric acid or derivatives of hydroxy acids such as pyruvic acid, methyl pyruvate, ethyl pyruvate, isopropyl pyruvate, benzoylformic acid, methyl benzoylformate, and ethyl benzoylformate.

Other embodiments employ ascorbic acid as a reductant, most preferably fat-soluble fatty acid esters of ascorbic acid (vitamin C) in addition to tocotrienol. The more oxidation-resistant saturated fatty acid esters of ascorbic acid are preferred, including, but not limited to, ascorbyl laurate, ascorbyl myristate, ascorbyl palmirate, ascorbyl stearate, and ascorbyl behenate. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmirate.

The combination of tocotrienol or tocotrienol-enriched vitamin E preparations and a fat-soluble vitamin C fatty acid ester in a dermatologically acceptable carrier is especially advantageous in compositions because tocotrienol augments the efficacy of the composition. The combination readily solubilizes in the lipid-rich layers of the skin and together scavenge free radicals involved in aging, inflammation, and other skin damage (more fully discussed below). As has been mentioned, it also contributes to the replacement of natural oils in hair compositions.

The effectiveness of tocotrienols and tocotrienol derivatives, especially when employed in combination with a reductant such as ascorbyl fatty acid esters, can be postulated as resulting from the antioxidant properties of tocotrienol per se, which properties are unexpectedly retained and provided to a high degree when used in concert with ascorbyl fatty acid esters when these are delivered in combination to the skin in an extremely effective manner in an oil phase. The mechanism of the effect is not well understood, but may be related to the anti-oxidant properties of the active compounds and/or their interference with chemical reactions.

In terms of a possible explanation for the effectiveness of tocotrienol in the prevention or treatment of damage to the skin, it is noted that tocotrienol, as an antioxidant, can scavenge free radicals such as the oxygen radicals created by exposure of skin cells to damage, as well as the generation of free radicals produced by normal metabolism extracellularly and intracellularly. Alpha-tocotrienol, as a powerful antioxidant concentrated in cell membranes, can lessen erythema by the mechanism of free radical scavenging and chain breaking chemical reactions. Ascorbic acid is a powerful reducing agent that can prevent oxidative damage and regenerate chromanoxyl radicals formed as vitamin E derivatives scavenge radicals, reforming vitamin E that can scavenge more radicals. Preferred embodiments of this invention harness this synergestic effect.

In addition, ascorbic acid can increase cyclo-oxygenase activity in human cells. Cyclo-oxygenase is a key enzyme in the oxidation of arachadonic acid, which leads the formation of prostaglandins which in turn mediate inflammation.

Because cell aging is the result of free radical damage, it is apparent that tocotrienols are also effective in the prevention of cell aging. The tocotrienols, with their unsaturated hydrocarbon chain, disperse within cell membranes, acting as a free radical scavenger and neutralizer, and prevent the cross-linking of cell membranes that is seen in the aging process. Once the cell membranes are cross-linked, the permeability of cell membranes increases, causing an inefficient exchange of nutrients and waste products within the cell. The decreased cell permeability results in increased ionic concentration of potassium, which then causes decreased messenger RNA production. The increased ionic concentration also interferes with enzyme activity, as enzymes are very much dependent on ionic concentration for their action.

In addition to decreased production of RNA, there is a marked decrease in the production of protein with aging, and therefore the cell cannot repair itself. The altered cellular membranes prevent removal of waste products in the cell, such as lipofucin, which is a histologic characteristic of all aging cells. Tocotrienol, by preventing free radical damage to cell membranes, and preventing decreased permeability to cells, can theoretically prevent aging of the cell by maintaining proper ionic concentration, proper disposal of waste products, and efficient protein and RNA production. Topical application of tocotrienols to skin can prevent cell aging.

The method of the present invention is particularly useful for the prevention of skin damage which may result from exposure to ultraviolet radiation, but, based upon the likely mechanism of action, also is useful in general for treatment of any radiation-induced skin damage, particularly that associated with free radical related damage. As such, the topical application of tocotrienol according to the invention can also be effective for chronic administration to prevent the free radical damage seen in the natural aging process of the skin and the free radical damage caused by chronic exposure to sunlight. Tocotrienol or tocotrienol and ascorbyl fatty acid esters can thus be added to dermatological creams and emollients as well as to commercial suncreens to enhance their anti-aging and anti-cancer activity.

It is an advantage of the invention that, because of the efficiency of free radical scavenging and other biochemical mechanisms involved after application of tocotrienol or tocotrienol and ascorbic acid fatty acid ester combinations to skin, compositions of the invention exhibit efficacy when applied to a variety of skin damaged conditions, including dry skin, psoriasis, and dermatitis (contact, irritant, and allergic). Compositions of the invention can also be used as a treatment after burn.

Tocotrienol compositions also ameloriate keratin oxidation by the same mechanisms described above for collagen. In hair compositions, its physical properties also enhance oil replacement in hair damaged by excessive sunlight or harsh chemicals.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates the contrary.

All references cited herein are expressly incorporated herein in their entireties by reference.

I claim:

1. A method for treating or preventing skin damage, said method comprising topically applying to skin areas subject to such damage an effective amount of an active compound selected from the group consisting of tocotrienols in the substantial absence of tocopherols, vitamin E preparations enriched with tocotrienols, and mixtures thereof.

2. A method according to claim 1 wherein the active compound is a tocotrienol selected from the group consisting of alpha-tocotrienol, beta-tocotrienol, gamma-tocotrienol, delta-tocotrienol, desmethyl-tocotrienol, didesmethyl-tocotrienol, and mixtures thereof.

3. A method according to claim 1 wherein said effective amount is appied as a composition further comprising a reductant.

4. A method according to claim 3 wherein said reductant is a fat-soluble fatty acid ester of ascorbic acid.

5. A method according to claim 4 wherein said fat-soluble fatty acid ester of ascorbic acid is selected from the group consisting of ascorbyl palmitate, ascorbyl laurate, ascorbyl myristate, ascorbyl stearate, and mixtures thereof.

6. A method according to claim 5 wherein said fat-soluble fatty acid ester of ascorbic acid is ascorbyl palmitate.

7. A method according to claim 1 wherein the composition comprises about 0.025% to about 10% by weight tocotrienol.

8. A method according to claim 1 wherein said skin damage is selected from the group consisting of inflammation, dry skin, aging, psoriasis, dermatitis, and burn.

9. A method according to claim 1 wherein the effective amount comprises an amount effective, in the lipid-rich layers of the skin, to scavenge free radicals in the skin.

10. A method for the treatment or prevention of hair damage, said treatment comprising topically applying to the affected hair an effective amount of a composition comprised of a dermatologically acceptable carrier and a tocotrienol composition selected from the group consisting of (a) a tocotrienol selected from the group consisting of tocotrienols, derivatives of tocotrienols, and mixtures thereof, containing essentially no tocopherols bearing saturated hydrocarbon tails, (b) a vitamin E preparation enriched with a tocotrienol selected from the group consisting of tocotrienols, derivatives of tocotrienols, and (c) mixtures thereof.

11. A method according to claim 10 wherein the composition further comprises a fat-soluble fatty acid ester of ascorbic acid selected from the group consisting of ascorbyl palmirate, ascorbyl laurate, ascorbyl myristate, ascorbyl stearate, and mixtures thereof.

12. A method according to claim 11 wherein the tocotrienol is selected from the group consisting of alpha-tocotrienol, beta-tocotrienol, gamma-tocotrienol, delta-tocotrienol, desmethyl-tocotrienol, didesmethyl-tocotrienol, and mixtures thereof.

13. A method according to claim 12 wherein the tocotrienol is alpha-tocotrienol.

14. In a dermatological composition for treatment of inflammation or aging of the skin in a dermatologically acceptable carrier, an improvement wherein, to augment the efficacy of the composition, said composition further comprises a tocotrienol composition selected from the group consisting of naturally occurring tocotrienols which contain essentially no tocopherol, vitamin E preparations enriched with naturally occurring tocotrienols, and mixtures thereof.

15. An improvement according to claim 14 wherein said tocotrienol is selected from the group consisting of alpha-tocotrienol, beta-tocotrienol, gamma-tocotrienol, and delta-tocotrienol.

16. An improvement according to claim 15 wherein said tocotrienol is D-alpha-tocotrienol.

17. An improvement according to claim 14 wherein said tocotrienol is present in said composition in amounts effective to scavenge free radicals from lipid-rich layers of the skin.

18. An improvement according to claim 15 wherein the composition further comprises a fat-soluble fatty acid ester of ascorbic acid selected from the group consisting of ascorbyl palmirate, ascorbyl laurate, ascorbyl myristate, ascorbyl stearate, and mixtures thereof.

19. An improvement according to claim 18 wherein said tocotrienol is present in said composition in amounts effective to scavenge free radicals from lipid-rich layers of the skin.

20. An improvement according to claim 14 wherein said composition comprises about 0.025% to about 3% by weight tocotrienol.

* * * * *